United States Patent
Brand et al.

(10) Patent No.: US 9,475,743 B2
(45) Date of Patent: Oct. 25, 2016

(54) PROCESS FOR THE PREPARATION OF SUBSTITUTED TRIS(2-HYDROXYPHENYL)METHANE

(71) Applicant: Wintershall Holding GmbH, Kassel (DE)

(72) Inventors: Fabien Jean Brand, Huningue (FR); Peter Hänggi, Giffers (CH); Michèle Gerster, Binningen (CH); Markus Hansch, Speyer (DE)

(73) Assignee: Wintershall Holding GmbH, Kassel (DE)

( * ) Notice: Subject to any disclaimer, the term of this patent is extended or adjusted under 35 U.S.C. 154(b) by 0 days.

(21) Appl. No.: 14/773,003

(22) PCT Filed: Feb. 28, 2014

(86) PCT No.: PCT/EP2014/053945
§ 371 (c)(1),
(2) Date: Sep. 4, 2015

(87) PCT Pub. No.: WO2014/139808
PCT Pub. Date: Sep. 18, 2014

(65) Prior Publication Data
US 2016/0016871 A1  Jan. 21, 2016

(30) Foreign Application Priority Data
Mar. 13, 2013 (EP) .................... 13158916

(51) Int. Cl.
*C07C 37/11* (2006.01)
(52) U.S. Cl.
CPC ................... *C07C 37/11* (2013.01)
(58) Field of Classification Search
CPC ....................................................... C07C 37/11
See application file for complete search history.

(56) References Cited

U.S. PATENT DOCUMENTS

| 9,039,791 B2 | 5/2015 | Peretolchin et al. |
| 9,062,266 B2 | 6/2015 | Peretolchin et al. |
| 2013/0098609 A1 | 4/2013 | Oetter et al. |
| 2013/0133243 A1 | 5/2013 | Roger-Gopfert et al. |
| 2013/0228332 A1 | 9/2013 | Maitro-Vogel et al. |
| 2013/0232858 A1 | 9/2013 | Strittmatter et al. |
| 2013/0296210 A1 | 11/2013 | Hansch et al. |
| 2014/0005310 A1 | 1/2014 | Gerseter et al. |
| 2014/0011715 A1 | 1/2014 | Boehn et al. |
| 2014/0045980 A1 | 2/2014 | Gerster et al. |
| 2014/0303304 A1 | 10/2014 | Frost et al. |
| 2015/0266808 A1 | 9/2015 | Hansch et al. |

FOREIGN PATENT DOCUMENTS

| WO | WO-2012/123928 | 9/2012 |
| WO | WO-2012/147025 | 11/2012 |
| WO | WO-2013/000997 | 1/2013 |
| WO | WO-2013/056843 | 4/2013 |
| WO | WO-2013/057044 | 4/2013 |
| WO | WO-2013/064689 | 5/2013 |
| WO | WO-2013/076006 | 5/2013 |
| WO | WO-2013/087701 | 6/2013 |
| WO | WO-2013/117616 | 8/2013 |
| WO | WO-2013/127629 | 9/2013 |
| WO | WO-2013/131800 | 9/2013 |
| WO | WO-2013/131837 | 9/2013 |
| WO | WO-2013/174631 | 11/2013 |
| WO | WO-2014/005861 | 1/2014 |
| WO | WO-2014/064151 | 5/2014 |
| WO | WO-2014/083102 | 6/2014 |
| WO | WO-2014/139808 | 9/2014 |
| WO | WO-2014/139935 | 9/2014 |

OTHER PUBLICATIONS

Casiraghi et al. ("Regiospecific Reactions of Phenol Salts: Reaction-Pathways of Alkylphenoxy-magesiumhalides with Triethylorthoformate", Tetrahedron Letters, No. 9, 1973, pp. 679-682).*
PCT International Preliminary Report on Patentability on PCT/EP/2014/053945, dated Sep. 15, 2015, 4 pages.
PCT International Search Report in PCT/EP2014/053945, mailed Apr. 8, 2014, 2 pages.
PCT International Written Opinion in PCT/EP2014/053945, mailed Apr. 8, 2014, 3 pages.
Dinger, Maarten B., et al., Extended Structures Built on a Triphenoxymethane Platform—C3-Symmetric, Conformational Mimics of Calix[n]arenes, *European Journal of Organic Chemistry*, vol. 2000, Issue 13 2000, 2467-2478, 2 pages.

* cited by examiner

*Primary Examiner* — Rosalynd Keys
(74) *Attorney, Agent, or Firm* — Servilla Whitney LLC

(57) ABSTRACT

Described is a novel process for the preparation of substituted tris(2-hydroxyphenyl)methane derivatives and the use of tris(2-hydroxyphenyl)methane derivatives for tertiary mineral oil production.

14 Claims, No Drawings

PROCESS FOR THE PREPARATION OF SUBSTITUTED TRIS(2-HYDROXYPHENYL)METHANE

CROSS-REFERENCE TO RELATED APPLICATIONS

This is application is the National Stage Entry of PCT/EP2014/053945, filed Feb. 28, 2014, which claims priority to European Application No. 13158916.0, filed Mar. 13, 2013, the disclosures of which are incorporated herein by reference in their entireties.

TECHNICAL FIELD

The presently claimed invention is directed to a process for the preparation of substituted tris(2-hydroxyphenyl) methane derivatives and the use of tris(2-hydroxyphenyl) methane derivatives for tertiary mineral oil production.

BACKGROUND

In natural mineral oil deposits, mineral oil is often present in the cavities of porous reservoir rocks which are sealed toward the surface of the earth by impervious overlying strata. The cavities may be very fine cavities, capillaries or pores. Fine pore necks may, for example, have a diameter of only approximately 1 μm. As well as mineral oil and proportions of natural gas, the deposits often also comprise salt-containing water. More particularly, the use of assistants for mineral oil production from salt-rich rock formations may be difficult.

In mineral oil production, a distinction is made between primary, secondary and tertiary production. In primary production, the mineral oil flows, after commencement of drilling of the deposit, of its own accord through the borehole to the surface due to the autogenous pressure of the deposit. The autogenous pressure results from the load on the essentially water-filled overlying rock strata. However, the autogenous deposit pressure often declines rapidly in the course of withdrawal of mineral oil, and so it is usually possible to produce only approx. 5 to 10% of the amount of mineral oil present in the deposit by means of primary production, according to the deposit. Thereafter, the autogenous pressure is no longer sufficient for production of mineral oil, and so pumps are often used thereafter for further mineral oil production.

After primary production, secondary production can therefore be used, in which, in addition to the boreholes which serve for production of the mineral oil, called the production wells, further boreholes are drilled into the mineral oil-bearing formation. These are called injection wells and are used to inject water into the deposit (called "water flooding"), in order to maintain the pressure or increase it again.

As a result of the injection of water or of a corresponding aqueous formulation, the mineral oil is also forced gradually through the cavities in the formation, preceding from the injection well in the direction of the production well. However, this only works for as long as the relatively high-viscosity oil is pushed onward by the water. As soon as the mobile water breaks through to the production wells along preferred flow paths, it flows on the path of least resistance from this time, i.e. particularly through the flow paths formed, and barely displaces any oil. By means of primary and secondary production, generally only approx. 30 to 35% of the amount of mineral oil present in the deposit can be produced.

After the measures of secondary mineral oil production (or after measures of primary mineral oil production), measures for tertiary mineral oil production (also known as "enhanced oil recovery", EOR) are also used to further enhance the oil yield. These include processes in which suitable chemicals, such as surfactants and/or polymers, are used as assistants in formulations for oil production. An overview of tertiary oil production using chemicals can be found, for example, in an article by D. G. Kessel from 1989 (Journal of Petroleum Science and Engineering, 2 (1989), 81 to 101).

One of the known techniques for tertiary mineral oil production is that known as "polymer flooding", in which an aqueous solution of a thickening polymer is injected into the mineral oil deposit through the injection wells, the viscosity of the aqueous polymer solution being matched to the viscosity of the mineral oil. Instead of a polymer solution, it is also possible to use aqueous solutions comprising non-polymeric thickeners.

Thickeners are chemicals which increase the viscosity of aqueous solutions, extending as far as gel formation. The injection of a thickened solution forces the mineral oil through the cavities in the formation preceding from the injection well in the direction of the production well, and allows the mineral oil to be produced through the production well. The fact that a thickener formulation has about the same mobility as the mineral oil reduces the risk that the formulation breaks through to the production well without having any effect ("fingering").

Thus, it is possible with thickener to mobilize the mineral oil much more homogeneously and efficiently than in the case of use of mobile water, by avoiding the occurrence of "fingering" in the case of use of water. Furthermore, piston-like displacement of the oil is achieved by the matching of the mobility. This accelerates the production of the mobile oil with regard to water flooding.

In addition, in the case of tertiary mineral oil production, it is also possible to use surfactants in addition to thickeners. Surfactants are used in mineral oil production in order to lower the oil-water interfacial tension to very low values and thus to mobilize further mineral oil which would otherwise remain in the rock.

The subsequent injection of a thickened water solution forces the mineral oil thus mobilized, as in the case of water flooding, preceding from the injection well in the direction of the production well, thus allowing it to be produced through the production well. Details of flooding with thickened or surfactant-containing solutions and components suitable therefor are described, for example, in "Petroleum, Enhanced Oil Recovery" (Kirk-Othmer, Encyclopedia of Chemical Technology, John Wiley & Sons, 2005).

In some cases, such a combination of successive "surfactant flooding" and "polymer flooding" is preceded by a phase involving an alkaline agent such as sodium hydroxide solution, in order to mobilize natural surfactants present in the crude oil ("alkaline polymer-surfactant flooding"). For the aforementioned combination of successive "surfactant flooding" and "polymer flooding", it is also possible to use what are called viscoelastic surfactants. These viscoelastic surfactants are interface-active substances which, in solution, form associates which increase the viscosity of the solution.

For examples thereof, reference is made to "Molecular Gels: Materials with Self-Assembled Fibrillar Networks"

(Richard G. Weiss, Pierre Terech, Dec. 22, 2005), Advances in Colliod and Interface Science 128-130 (2006) 77-102). With viscoelastic surfactants, it is possible to achieve a reduction in interfacial tension which cannot be achieved with polymeric components alone. Thickening surfactants for mineral oil production are described in various places. "Oilfield Reviews" (Vol. 16(4) (2004) 10-28) describes the use of viscoelastic surfactant systems as "fracturing fluids". As early as 1985, V. Shvets described the stabilization of suspensions by the use of nonionic surfactants (Journal of Applied Chemistry of USSR, 58 (6), 1985, 1220-1224).

The so-called associates that surfactants can form are also called micelles and form due to hydrophobic interactions.

The thickening properties of such solutions can generally be eliminated by shear, in which case the associates fall apart into smaller fragments. This operation, however, does not break any chemical bonds, and the associates develop their full thickening action again in the absence of shear.

This is an advantage of viscoelastic surfactant systems, more particularly over synthetic polymeric thickeners, which can be destroyed irreversibly by strong shear, for example in the course of pumping of a solution into an oil reservoir. An additional effect is the fact that viscoelastic surfactants lower the water-oil interfacial tension, which is the case only to a distinctly lesser degree, if at all, for polymers.

However, in order to develop viscoelastic surfactant systems that can economically be used on a large scale for enhanced oil recovery, it is necessary to develop a short route to tris(2-hydroxyphenyl)methane derivatives that is both economical and non-toxic.

G. Casiraghi et al. [Tetrahedron Letters, No. 9, 679-682 (1973)] describe the synthesis of tris(2-hydroxyphenyl) methane derivatives by reacting alkylphenoxy magnesium halides with triethylorthoformiate. The reaction is effected by deprotonation of the phenol derivatives with a Grignard reagent and subsequent addition of triethylorthoformiate to afford tris-phenoxides. This reaction is also described in Dinger et al. [Eur. J. Org. Chem. 2000, 2467 2478].

The main disadvantages ensuing from synthesizing tris (2-hydroxyphenyl)methane derivatives by using Grignard reagents are the general hazardousness of these reagents and the large amounts of different solvents that have to be used in order to keep the Grignard reagents in solution.

Another disadvantage of this protocol is the evolution of flammable ethane gas upon generation of the magnesium salt by treatment of the phenol derivative with EtMgBr. Additionally, the use of stoichiometric amounts of magnesium with respect to the phenol is a disadvantage.

Hence, there is still a need to provide a process for the preparation of tris(2-hydroxyphenyl)methane derivatives via a short route with good overall yield under environmentally acceptable conditions, i.e. by avoiding large amounts of potentially toxic organic solvents.

SUMMARY

Embodiments of a first aspect of the present invention are directed to a process. A first embodiment is directed to a process for the preparation of a compound of general formula (I)

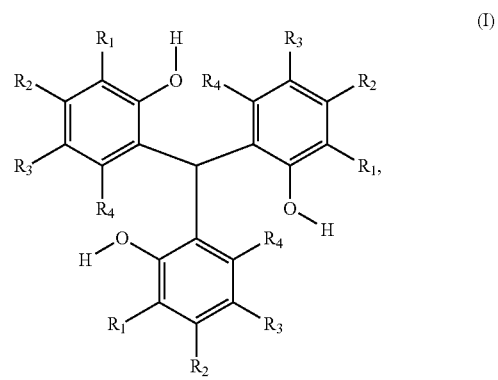

wherein $R^1$, $R^2$, $R^3$ and $R^4$, mutually independently, in each case denote H; F; Cl; Br; I; —OH; —NO$_2$; —CN; —C(=O)—R$^6$; —C(=O)—O—R$^7$; —O—C(=O)—R$^8$; —NH—C(=O)—R$^9$; —C(=O)—NH$_2$; —C(=O)—NH—R$^{10}$; —C(=O)—NR$^{11}$R$^{12}$; —O—R$^{13}$; —S—R$^{14}$; —S(=O)—R$^{15}$; —S(=O)$_2$—R$^{16}$; unsubstituted or at least monosubstituted alkyl; unsubstituted or at least monosubstituted heteroalkyl; unsubstituted or at least monosubstituted cycloalkyl; unsubstituted or at least monosubstituted cycloalkenyl; unsubstituted or at least monosubstituted heterocycloalkyl; unsubstituted or at least monosubstituted heterocycloalkenyl or unsubstituted or mono- or polysubstituted aryl; and $R^6$, $R^7$, $R^8$, $R^9$, $R^{10}$, $R^{11}$, $R^{12}$, $R^{13}$, $R^{14}$, $R^{15}$ and $R^{16}$, mutually independently, in each case denote unsubstituted or at least monosubstituted alkyl; unsubstituted or at least monosubstituted alkenyl or unsubstituted or at least monosubstituted heteroalkyl; the process comprising at least the step of reacting at least one compound of general formula (II)

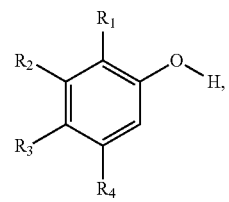

wherein $R^1$, $R^2$, $R^3$ and $R^4$, mutually independently, in each case denote H; F; Cl; Br; I; —OH; —NO$_2$; —CN; —C(=O)—R$^6$; —C(=O)—O—R$^7$; —O—C(=O)—R$^8$; —NH—C(=O)—R$^9$; —C(=O)—NH$_2$; —C(=O)—NH—R$^{10}$; —C(=O)—NR$^{11}$R$^{12}$; —O—R$^{13}$; —S—R$^{14}$; —S(=O)—R$^{15}$; —S(=O)$_2$—R$^{16}$; unsubstituted or at least monosubstituted alkyl; unsubstituted or at least monosubstituted heteroalkyl; unsubstituted or at least monosubstituted cycloalkyl; unsubstituted or at least monosubstituted cycloalkenyl; unsubstituted or at least monosubstituted heterocycloalkyl; unsubstituted or at least monosubstituted heterocycloalkenyl; or unsubstituted or mono- or polysubstituted aryl; and $R^6$, $R^7$, $R^8$, $R^9$, $R^{10}$, $R^{11}$, $R^{12}$, $R^{13}$, $R^{14}$, $R^{15}$ and $R^{16}$, mutually independently, in each case denote unsubstituted or at least monosubstituted alkyl; unsubstituted or at least monosubstituted alkenyl or unsubstituted or at least monosubstituted heteroalkyl; with at least one compound of general formula (III)

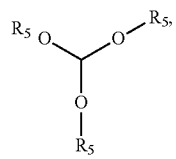

(III)

wherein $R^5$, mutually independently, in each case denotes unsubstituted or at least monosubstituted alkyl; in the presence of at least one Lewis acid.

In a second embodiment, the process of the first embodiment is modified, wherein the at least one Lewis acid is a metal-containing compound selected from the group consisting of (a) $AsX_3$, $GaX_3$, $BX_3$, $BX_3.(C_2H_5)_2O$, $BX_3.S(CH_3)_2$, $AlX_3$, $(C_2H_5)_2AlX$, $SbX_3$, $SbX_5$, $SnX_2$, $MgX_2$, $MgX_2.O(C_2H_5)_2$, $ZnX_2$, $BiX_3$, $FeX_2$, $TiX_2$, $TiX_4$, $NbX_5$, $NiX_2$, $CoX_2$, $HgX_2$, wherein X in each case denotes F, Cl, Br or I, (b) $BH_3$, $B(CH_3)_3$, $GaH_3$, $AlH_3$, $Al(acetate)(OH)_2$, $Al[OCH(CH_3)_2]_3$, $Al(OCH_3)_3$, $Al(OC_2H_5)$, $Al_2O_3$, $(CH_3)_3Al$, $Ti[OCH(CH_3)_2]_3Cl$, $Ti[OCH(CH_3)_2]_4$, methylaluminum di-(2,6-di-tert-butyl-4-methylphenoxide), methylaluminum di-(4-brom-2,6-di-tert-butylphenoxide), $LiClO_4$, (c) $Mg(acetate)_2$, $Zn(acetate)_2$, $Ni(acetate)_2$, $Ni(NO_3)_2$, $Co(acetate)_2$, $Co(NO_3)_2$, $Cu(acetate)_2$, $Cu(NO_3)_2$, Li(acetate), $Zr(acetylacetonate)_4$, $Si(acetate)_4$, K(acetate), Na(acetate), Cs(acetate), Rb(acetate), $Mn(acetate)_2$, $Fe(acetate)_2$, $Bi(acetate)_3$, $Sb(acetate)_3$, $Sr(acetate)_2$, $Sn(acetate)_2$, $Zr(acetate)_2$, $Ba(acetate)_2$, $Hg(acetate)_2$, Ag(acetate), $Tl(acetate)_3$, (d) $Sc(fluoromethansulfonate)_3$, $Ln(fluoromethanesulfonate)_3$, $Ni(fluoromethanesulfonate)_2$, $Ni(tosylate)_2$, $Co(fluoromethanesulfonate)_2$, $Co(tosylate)_2$, $Cu(fluoromethanesulfonate)_2$, and $Cu(tosylate)_2$.

In a third embodiment, the process of the first and second embodiments is modified, wherein the at least one Lewis acid is a metal-containing compound selected from the group consisting of $AlX_3$, $SnX_2$, $MgX_2$, $ZnX_2$, $BiX_3$, $FeX_2$, $Al[OCH(CH_3)_2]_3$, $Al(OCH_3)_3$ and $Al(OC_2H_5)_3$, wherein X in each case denotes F, Cl, Br, or I.

In a fourth embodiment, the process of the first through third embodiments is modified, wherein X denotes Cl.

In a fifth embodiment, the process of the first through fourth embodiments is modified, wherein the at least one Lewis acid is a metal-containing compound selected from the group consisting of $AlCl_3$, $SnCl_2$, $MgCl_2$, $ZnCl_2$, $BiCl_3$, $FeCl_2$, $Al[OCH(CH_3)_2]_3$, $Al(OCH_3)_3$, and $Al(OC_2H_5)_3$.

In a sixth embodiment, the process of the first embodiment is modified, wherein the molar ratio of the at least one compound of general formula (II) to the at least one compound of general formula (III) is in the range of 5.0:1.0 and 2.5:1.0.

In a seventh embodiment, the process of the first embodiment is modified, wherein the concentration of the at least one metal-containing compound in relation to the at least one compound of general formula (II) is in the range of 1 mol-% to 60 mol-%.

In an eighth embodiment, the process of the first through seventh embodiments is modified, wherein the at least one compound of general formula (II) and the at least one compound of general formula (III) are reacted in at least one inert organic solvent selected from the group consisting of toluene, xylene, ortho-xylene, para-xylene, mesitylene, cyclohexane, cyclopentanone, benzonitrile, chlorobenzene, 1,2-dichlorobenzene, 1,2-dichloroethane, dibutylether, anisol, butylacetate, methylethylketone, methylisobutylketone, pinacolone, dimethylformamide, and acetonitrile.

In a ninth embodiment, the process of the first through eighth embodiments is modified, wherein the at least one compound of general formula (II) and the at least one compound of general formula (III) are reacted at a temperature in the range of 70° C. to 140° C. for a period in the range of 2 to 20 hours.

In a tenth embodiment, the process of the first through ninth embodiments is modified, wherein the at least one compound of general formula (II) and the at least one compound of general formula (III) are reacted in an inert solvent, wherein the molar concentration of the at least one compound of general formula (II) is in the range of 1.0 M to 8.0 M.

In an eleventh embodiment, the process of the first through tenth embodiments is modified, wherein $R^5$ denotes unsubstituted $C_{1-5}$ alkyl.

In a twelfth embodiment, the process of the first through eleventh embodiments is modified, wherein $R^1$ and $R^3$, mutually independently, in each case denote H, F, Cl, Br, I, unsubstituted or at least monosubstituted $C_{1-12}$ alkyl, unsubstituted or at least monosubstituted $C_{3-8}$ cycloalkyl, or unsubstituted or mono- or polysubstituted aryl; and $R^2$ and $R^4$, in each case denote H.

In a thirteenth embodiment, the process of the first through twelfth embodiments is modified, wherein $R^1$ and $R^3$, mutually independently, in each case denote a moiety selected from the group consisting of methyl, ethyl, propyl, isopropyl, n-butyl, isobutyl, tert-butyl, n-pentyl, 1,1-dimethylpropyl, 2,2-dimethylpropyl, 3-methylbutyl, hexyl, 2-ethylhexyl, heptyl, octyl, nonyl, decyl, undecyl, dodecyl, cyclopentyl, cyclohexyl, 1,1,3,3,-tetramethylbutyl, sec-butyl, $CH_3$—$CH_2$—$C(CH_3)_2$—, and unsubstituted phenyl; and $R^2$ and $R^4$, in each case denote H.

In a fourteenth embodiment, the process of the first through thirteenth embodiments is modified, wherein the compound of general formula (I) is purified and isolated by applying the following steps: (a) adding an inert organic solvent and water to provide an organic phase and a water phase; (b) separating the organic phase from the water phase; (c) optionally washing the organic phase with a 1N aqueous solution of hydrochloric acid; (d) washing the organic phase with water; (e) filtering the organic phase to provide a residue and drying the residue.

DETAILED DESCRIPTION

Provided is a process for the preparation of tris(2-hydroxyphenyl)methane derivatives via a short route with good overall yield under environmentally acceptable conditions, i.e. by avoiding large amounts of potentially toxic organic solvents.

More specifically, provided is a process for the preparation of a compound of general formula (I)

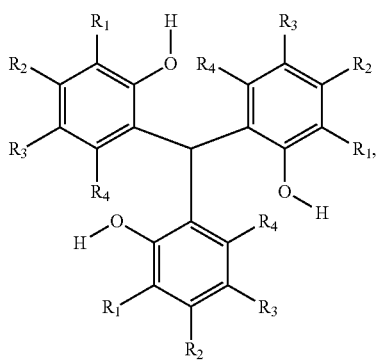

(I)

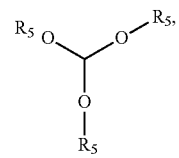

(III)

wherein $R^1$, $R^2$, $R^3$ and $R^4$, mutually independently, in each case denote H; F; Cl; Br; I; —OH; —NO$_2$; —CN; —C(=O)—R$^6$; —C(=O)—O—R$^7$; —O—C(=O)—R$^8$; —NH—C(=O)—R$^9$; —C(=O)—NH$_2$; —C(=O)—NH—R$^{10}$; —C(=O)—NR$^{11}$R$^{12}$; —O—R$^{13}$; —S—R$^{14}$; —S(=O)—R$^{15}$; —S(=O)$_2$—R$^{16}$; unsubstituted or at least monosubstituted alkyl; unsubstituted or at least monosubstituted heteroalkyl; unsubstituted or at least monosubstituted cycloalkyl; unsubstituted or at least monosubstituted cycloalkenyl; unsubstituted or at least monosubstituted heterocycloalkyl; unsubstituted or at least monosubstituted heterocycloalkenyl; or unsubstituted or mono- or polysubstituted aryl;
and
$R^6$, $R^7$, $R^8$, $R^9$; $R^{10}$; $R^{11}$; $R^{12}$; $R^{13}$; $R^{14}$; $R^{15}$ and $R^{16}$, mutually independently, in each case denote unsubstituted or at least monosubstituted alkyl; unsubstituted or at least monosubstituted alkenyl or unsubstituted or at least monosubstituted heteroalkyl;
comprising at least the step of reacting at least one compound of general formula (II)

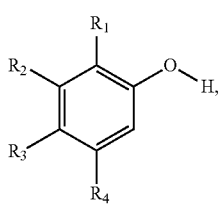

(II)

wherein $R^1$, $R^2$, $R^3$ and $R^4$, mutually independently, in each case denote H; F; Cl; Br; I; —OH; —NO$_2$; —CN; —C(=O)—R$^6$; —C(=O)—O—R$^7$; —O—C(=O)—R$^8$; —NH—C(=O)—R$^9$; —C(=O)—NH$_2$; —C(=O)—NH—R$^{10}$; —C(=O)—NR$^{11}$R$^{12}$; —O—R$^{13}$; —S—R$^{14}$; —S(=O)—R$^{15}$; —S(=O)$_2$—R$^{16}$; unsubstituted or at least monosubstituted alkyl; unsubstituted or at least monosubstituted heteroalkyl; unsubstituted or at least monosubstituted cycloalkyl; unsubstituted or at least monosubstituted cycloalkenyl; unsubstituted or at least monosubstituted heterocycloalkyl; unsubstituted or at least monosubstituted heterocycloalkenyl; or unsubstituted or mono- or polysubstituted aryl;
and
$R^6$, $R^7$, $R^8$, $R^9$, $R^{10}$, $R^{11}$, $R^{12}$, $R^{13}$, $R^{14}$, $R^{15}$ and $R^{16}$, mutually independently, in each case denote unsubstituted or at least monosubstituted alkyl; unsubstituted or at least monosubstituted alkenyl or unsubstituted or at least monosubstituted heteroalkyl;
with at least one compound of general formula (III)

wherein $R^5$, mutually independently, in each case denotes unsubstituted or at least monosubstituted alkyl;
in the presence of at least one Lewis acid,
wherein
the above-stated alkyl residues are in each case branched or straight-chain and comprise 1, 2, 3, 4, 5, 6, 7, 8, 9, 10, 11 or 12 carbon atoms as chain links;
the above-stated alkenyl residues are in each case branched or straight-chain and comprise 2, 3, 4, 5, 6, 7, 8, 9, 10, 11 or 12 carbon atoms as chain links;
the above-stated heteroalkyl residues are in each case 3-, 4-, 5-, 6-, 7-, 8-, 9-, 10-, 11- or 12-membered;
the above-stated heteroalkyl residues comprise 1, 2, or 3 heteroatom(s) mutually independently selected from the group consisting of oxygen, sulfur and nitrogen as chain link(s);
the above-stated alkyl residues, alkenyl residues and heteroalkyl residues may be substituted in each case with optionally 1, 2, 3, 4 or 5 substituents mutually independently selected from the group consisting of F, Cl, Br, I, —NO$_2$, —CN, —OH, —SH, —NH$_2$, —N(C$_{1-5}$-alkyl)$_2$, —N(C$_{1-5}$-alkyl) (phenyl), —N(C$_{1-5}$-alkyl)(CH$_2$-phenyl), —N(C$_{1-5}$-alkyl)(CH$_2$—CH$_2$-phenyl), —C(=O)—H, —C(=O)—C$_{1-5}$-alkyl, —C(=O)-phenyl, —C(=S)—C$_{1-5}$-alkyl, —C(=S)-phenyl, —C(=O)—OH, —C(=O)—O—C$_{1-5}$-alkyl, —C(=O)—O-phenyl, —C(=O)—NH$_2$, —C(=O)—NH—C$_{1-5}$-alkyl, —C(=O)—N(C$_{1-5}$-alkyl)$_2$, —S(=O)—C$_{1-5}$-alkyl, —S(=O)-phenyl, —S(=O)$_2$—C$_{1-5}$-alkyl, —S(=O)$_2$-phenyl, —S(=O)$_2$—NH$_2$ and —SO$_3$H, wherein the above-stated-C$_{1-5}$ alkyl residues may in each case be linear or branched and the above-stated phenyl residues may, in one or more embodiments, be substituted with 1, 2, 3, 4 or 5 substituents mutually independently selected from the group consisting of F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, 2-butyl, isobutyl and tert.-butyl;
the above-stated cycloalkyl residues in each case comprise 3, 4, 5, 6, 7, 8, or 9 carbon atoms as ring members;
the above-stated cycloalkenyl residues in each case comprise 3, 4, 5, 6, 7, 8, or 9 carbon atoms as ring members;
the above-stated heterocycloalkyl residues are in each case 3-, 4-, 5-, 6-, 7-, 8-, or 9-membered;
the above-stated heterocycloalkenyl residues are in each case 4-, 5-, 6-, 7-, 8-, or 9-membered;
the above-stated aryl residues in each case comprise 6, 10, or 14 carbon atoms;
the above-stated heterocycloalkyl residues and heterocycloalkenyl residues in each case comprise 1, 2 or 3 heteroatom(s) mutually independently selected from the group consisting of oxygen, sulfur and nitrogen (NH) as ring member(s);

the above-stated aryl residues, cycloalkyl residues, cycloalkenyl residues, heterocycloalkyl residues and heterocycloalkenyl residues may be substituted in each case with optionally 1, 2, 3, 4 or 5 substituents mutually independently selected from the group consisting of F, Cl, Br, I, —CN, —$NO_2$, —OH, —SH, —$NH_2$, —C(=O)—OH, —$C_{1-5}$ alkyl, —($CH_2$)—O—$C_{1-5}$-alkyl, —$C_{2-5}$ alkenyl, —$C_{2-5}$ alkynyl, —C≡C—Si($CH_3$)$_3$, —C≡C—Si($C_2H_5$)$_3$, —S—$C_{1-5}$-alkyl, —S-phenyl, —S—$CH_2$-phenyl, —O—$C_{1-5}$-alkyl, —O-phenyl, —O—$CH_2$-phenyl, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —S(=O)$_2$-phenyl, —S(=O)$_2$—$C_{1-5}$-alkyl, —S(=O)—$C_{1-5}$-alkyl, —NH—$C_{1-5}$-alkyl, N($C_{1-5}$alkyl)$_2$, —C(=O)—O—$C_{1-5}$-alkyl, —C(=O)—H; —C(=O)—$C_{1-5}$-alkyl, —$CH_2$—O—C(=O)-phenyl, —O—C(=O)-phenyl, —NH—S(=O)$_2$—$C_{1-5}$-alkyl, —NH—C(=O)—$C_{1-5}$-alkyl, —C(=O)—$NH_2$, —C(=O)—NH—$C_{1-5}$-alkyl, —C(=O)—N($C_{1-5}$-alkyl)$_2$, pyrazolyl, phenyl, furyl (furanyl), thiazolyl, thiadiazolyl, thiophenyl (thienyl), benzyl and phenethyl, wherein the above-stated $C_{1-5}$ alkyl residues may in each case be linear or branched and the cyclic substituents or the cyclic residues of these substituents themselves may be substituted with optionally 1, 2, 3, 4, or 5, specifically with optionally 1, 2, 3, or 4, substituents mutually independently selected from the group consisting of F, Cl, Br, I, —CN, —$NO_2$, —OH, —SH, —$NH_2$, —C(=O)—OH, —$C_{1-5}$ alkyl, —($CH_2$)—O—$C_{1-5}$-alkyl, —$C_{2-5}$ alkenyl, —$C_{2-5}$ alkynyl, —C≡C—Si($CH_3$)$_3$, —C≡C—Si($C_2H_5$)$_3$, —S—$C_{1-5}$-alkyl, —S-phenyl, —S—$CH_2$-phenyl, —O—$C_{1-5}$-alkyl, —O-phenyl, —O—$CH_2$-phenyl, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$ and —S—$CH_2F$.

For the purposes of the present invention, the term "alkyl" covers acyclic saturated hydrocarbon residues, which may be branched or straight-chain and unsubstituted or at least monosubstituted with, as in the case of $C_{1-12}$ alkyl, 1 to 12 (i.e. 1, 2, 3, 4, 5, 6, 7, 8, 9, 10, 11, or 12) C atoms. If one or more of the substituents denote an alkyl residue or comprise an alkyl residue which is mono- or polysubstituted, this may be substituted with optionally 1, 2, 3, 4, or 5, specifically with 1, 2, or 3, substituents mutually independently selected from the group consisting of F, Cl, Br, I, —$NO_2$, —CN, —OH, —SH, —$NH_2$, —N($C_{1-5}$-alkyl)$_2$, —N($C_{1-5}$-alkyl)(phenyl), —N($C_{1-5}$-alkyl) ($CH_2$-phenyl), —N($C_{1-5}$-alkyl)($CH_2$—$CH_2$-phenyl), —C(=O)—H, —C(=O)—$C_{1-5}$-alkyl, —C(=O)-phenyl, —C(=S) —$C_{1-5}$-alkyl, —C(=S)-phenyl, —C(=O)—OH, —C(=O)—O—$C_{1-5}$-alkyl, —C(=O)—O-phenyl, —C(=O)—$NH_2$, —C(=O)—NH—$C_{1-5}$-alkyl, —C(=O)—N($C_{1-5}$-alkyl)$_2$, —S(=O)—$C_{1-5}$-alkyl, —S(=O)-phenyl, —S(=O)$_2$—$C_{1-5}$-alkyl, —S(=O)$_2$-phenyl, —S(=O)$_2$—$NH_2$ and —$SO_3H$, wherein the above-stated-$C_{1-5}$ alkyl residues may in each case be linear or branched and the above-stated phenyl residues may, in one or more embodiments, be substituted with 1, 2, 3, 4 or 5 substituents mutually independently selected from the group consisting of F, Cl, Br, I, —CN, —$CF_3$, —OH, —$NH_2$, —O—$CF_3$, —SH, —O—$CH_3$, —O—$C_2H_5$, —O—$C_3H_7$, methyl, ethyl, n-propyl, isopropyl, n-butyl, 2-butyl, isobutyl and tert.-butyl. In one or more embodiments, substituents may be selected mutually independently from the group consisting of F, Cl, Br, I, —$NO_2$, —CN, —OH, —SH, —$NH_2$, —N($CH_3$)$_2$, —N($C_2H_5$)$_2$ and N($CH_3$)($C_2H_5$).

The term "heteroalkyl" denotes an alkyl residue as described above, in which one or more C atoms have in each case been replaced by a heteroatom mutually independently selected from the group consisting of oxygen, sulfur and nitrogen (NH). In one or more embodiments, heteroalkyl residues comprise 1, 2, or 3 heteroatom(s) mutually independently selected from the group consisting of oxygen, sulfur and nitrogen (NH) as chain link(s). In one or more embodiments, heteroalkyl residues may be 3- to 12-membered.

Examples which may be mentioned of suitable heteroalkyl residues which may be unsubstituted or mono- or polysubstituted, are —$CH_2$—O—$CH_3$, —$CH_2$—O—$C_2H_5$, —$CH_2$—O—CH($CH_3$)$_2$, —$CH_2$—O—C($CH_3$)$_3$, —$CH_2$—S—$CH_3$, —$CH_2$—S—$C_2H_5$, —$CH_2$—S—CH($CH_3$)$_2$, —$CH_2$—S—C($CH_3$)$_3$, —$CH_2$—NH—$CH_3$, —$CH_2$—NH—$C_2H_5$, —$CH_2$—NH—CH($CH_3$)$_2$, —$CH_2$—NH—C($CH_3$)$_3$, —$CH_2$—$CH_2$—CO—$CH_3$, —$CH_2$—$CH_2$—O—$C_2H_5$, —$CH_2$—$CH_2$—O—CH($CH_3$)$_2$, —$CH_2$—$CH_2$—O—C($CH_3$)$_3$, —$CH_2$—$CH_2$—S—$CH_3$, —$CH_2$—$CH_2$—S—$C_2H_5$, —$CH_2$—$CH_2$—S—CH($CH_3$)$_2$, —$CH_2$—$CH_2$—S—C($CH_3$)$_3$, —$CH_2$—$CH_2$—NH—$CH_3$, —$CH_2$—$CH_2$—NH—$C_2H_5$, —$CH_2$—$CH_2$—NH—CH($CH_3$)$_2$, —$CH_2$—$CH_2$—NH—C($CH_3$)$_3$, —$CH_2$—S—$CH_2$—O—$CH_3$, —$CH_2$—O—$CH_2$—O—$C_2H_5$, —$CH_2$—O—$CH_2$—O—CH($CH_3$)$_2$, —$CH_2$—S—$CH_2$—O—C($CH_3$)$_3$, —$CH_2$—O—$CH_2$—S—$CH_3$, —$CH_2$—O—$CH_2$—S—$C_2H_5$, —$CH_2$—O—$CH_2$—S—CH($CH_3$)$_2$, —$CH_2$—NH—$CH_2$—S—C($CH_3$)$_3$, —$CH_2$—O—$CH_2$—NH—$CH_3$, —$CH_2$—O—$CH_2$—NH—$C_2H_5$, —$CH_2$—CO—$CH_2$—NH—CH($CH_3$)$_2$, —$CH_2$—S—$CH_2$—NH—C($CH_3$)$_3$ and —$CH_2$—$CH_2$—C(H)($CH_3$)—($CH_2$)$_3$—$CH_3$.

Examples of suitable substituted heteroalkyl residues which may be mentioned are —($CH_2$)—O—($CF_3$), —($CH_2$)—O—($CHF_2$), —($CH_2$)—O—($CH_2F$), —($CH_2$)—S—($CF_3$), —($CH_2$)—S—($CHF_2$), —($CH_2$)—S—($CH_2F$), —($CH_2$)—($CH_2$)—O—($CF_3$), —($CF_2$)—O—($CF_3$), —($CH_2$)—($CH_2$)—S—($CF_3$) and —($CH_2$)—($CH_2$)—($CH_2$)—O—($CF_3$).

For the purpose of the present invention, the term "alkenyl" covers acyclic unsaturated hydrocarbon residues, which may be branched or straight-chain and unsubstituted or at least mono-substituted and comprise at least one double bond, specifically 1, 2, or 3 double bonds, with, as in the case of $C_2$-$C_{12}$ alkenyl, 2 to 30 (i.e. 2, 3, 4, 5, 6, 7, 8, 9, 10, 11, 12) C atoms or with, as in the case of $C_2$-$C_6$ alkenyl, 2 to 6 (i.e. 2, 3, 4, 5, or 6) C atoms. If one or more of the substituents denote an alkenyl residue or comprise an alkenyl residue which is mono- or polysubstituted, this may be substituted with optionally 1, 2, 3, 4, or 5, more specifically with 1, 2 or 3, substituents mutually independently selected from the group consisting of F, Cl, Br, I, —$NO_2$, —CN, —OH, —SH, —$NH_2$, —N($C_{1-5}$-alkyl)$_2$, —N($C_{1-5}$-alkyl) (phenyl), —N($C_{1-5}$-alkyl)($CH_2$-phenyl), —N($C_{1-5}$-alkyl) ($CH_2$—$CH_2$-phenyl), —C(=O)—H, —C(=O)—$C_{1-5}$-alkyl, —C(=O)-phenyl, —C(=S)—$C_{1-5}$-alkyl, —C(=S)-phenyl, —C(=O)—OH, —C(=O)—O—$C_{1-5}$-alkyl, —C(=O)—O-phenyl, —C(=O)—$NH_2$, —C(=O)—NH—$C_{1-5}$-alkyl, —C(=O)—N($C_{1-5}$-alkyl)$_2$, —S(=O)—$C_{1-5}$-alkyl, —S(=O)-phenyl, —S(=O)$_2$—$C_{1-5}$-alkyl, —S(=O)$_2$-phenyl, —S(=O)$_2$—$NH_2$ and —$SO_3H$, wherein the above-stated-$C_{1-5}$ alkyl residues may in each case be linear or branched and the above-stated phenyl residues may be substituted with 1, 2, 3, 4, or 5 substituents mutually independently selected from the group consisting of F, Cl, Br, I, —CN, —$CF_3$, —OH, —$NH_2$, —O—$CF_3$, —SH, —O—$CH_3$, —O—$C_2H_5$, —O—$C_3H_7$, methyl, ethyl, n-propyl, isopropyl, n-butyl, 2-butyl, isobutyl, and tert.-butyl. In one or more embodiments, the substituents may be selected mutually independently from the group consisting of F, Cl, Br, I, —NO$_2$, —CN, —OH, —SH, —NH$_2$, —N(CH$_3$)$_2$, —N(C$_2$H$_5$)$_2$ and —N(CH$_3$)(C$_2$H$_5$).

For the purposes of the present invention, the term "cycloalkyl" means a cyclic saturated hydrocarbon residue, with, in one or more embodiments, 3, 4, 5, 6, 7, 8, or 9 C atoms, specifically with 3, 4, 5, 6, or 7 C atoms, very specifically with 5 or 6 C atoms, wherein the residue may be unsubstituted or monosubstituted or identically or differently polysubstituted. Examples which may be mentioned of suitable C$_{3-9}$ cycloalkyl residues which may be unsubstituted or mono- or polysubstituted are cyclopropyl, cyclobutyl, cyclopentyl, cyclohexyl, cycloheptyl, cyclooctyl and cyclononyl. Examples of suitable C$_{3-7}$ cycloalkyl residues which may be mentioned are cyclopropyl, cyclobutyl, cyclopentyl, cyclohexyl and cycloheptyl.

For the purposes of the present invention, the term "cycloalkenyl" means a cyclic unsaturated hydrocarbon residue with, in one or more embodiments, 3, 4, 5, 6, 7, 8, or 9 C atoms, specifically with 3, 4, 5, 6, or 7 C atoms, very specifically with 5 or 6 C atoms, which comprises at least one double bond, specifically one double bond, and may be unsubstituted or monosubstituted or identically or differently polysubstituted.

Examples which may be mentioned of suitable C$_{3-9}$ cycloalkenyl residues which may be unsubstituted or mono- or polysubstituted are cyclobutenyl, cyclopentenyl, cyclohexenyl, cycloheptenyl, cyclononenyl and cyclooctenyl. Examples of suitable C$_{5-6}$ cycloalkenyl residues which may be mentioned are cyclopentenyl and cyclohexenyl.

For the purposes of the present invention, the term "heterocycloalkyl" means a cyclic saturated hydrocarbon residue with, in one or more embodiments, 3, 4, 5, 6, 7, 8, or 9 C atoms, specifically with 3, 4, 5, 6, or 7 C atoms, very specifically with 5 or 6 C atoms, in which one or more C atoms have in each case been replaced by a heteroatom mutually independently selected from the group consisting of oxygen, sulfur and nitrogen (NH). In one or more embodiments, heterocycloalkyl residues may comprise 1, 2, or 3 heteroatom(s) mutually independently selected from the group consisting of oxygen, sulfur and nitrogen (NH) as ring member(s). A heterocycloalkyl residue may be unsubstituted or monosubstituted or identically or differently polysubstituted. In one or more embodiments, heterocycloalkyl residues may be 3- to 9-membered, specifically 3- to 7-membered, very specifically 5- to 7-membered.

Examples which may be mentioned of suitable 3- to 9-membered heterocycloalkyl residues which may be unsubstituted or mono- or polysubstituted are imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, azepanyl, azocanyl, diazepanyl, dithiolanyl, (1,3)-dioxolan-2-yl, isoxazolidinyl, isothioazolidinyl, pyrazolidinyl, oxazolidinyl, (1,2,4)-oxadiazolidinyl, (1,2,4)-thiadiazolidinyl, (1,2,4)-triazolidin-3-yl, (1,3,4)-thia-diazolidin-2-yl, (1,3,4)-triazolidin-1-yl, (1,3,4)-triazolidin-2-yl, tetrahydropyridazinyl, tetrahydropyrimidinyl, tetrahydropyrazinyl, (1,3,5)-tetrahydrotriazinyl, (1,2,4)-tetrahydrotriazin-1-yl, (1,3)-dithian-2-yl and (1,3)-thiazolidinyl. Examples of suitable 5- to 7-membered heterocycloalkyl residues which may be mentioned are imidazolidinyl, tetrahydrofuranyl, tetrahydrothiophenyl, pyrrolidinyl, piperidinyl, morpholinyl, piperazinyl, thiomorpholinyl, tetrahydropyranyl, oxetanyl, azepanyl, diazepanyl and (1,3)-dioxolan-2-yl.

For the purposes of the present invention, the term "heterocycloalkenyl" means a cyclic unsaturated hydrocarbon residue with, in one or more embodiments, 4, 5, 6, 7, 8, or 9 C atoms, specifically with 4, 5, 6, or 7 C atoms, very specifically with 5 or 6 C atoms, which comprises at least one double bond, specifically one double bond, and in which one or more C atoms have in each case been replaced by a heteroatom mutually independently selected from the group consisting of oxygen, sulfur and nitrogen (NH). In one or more embodiments, teterocycloalkenyl residues may comprise 1, 2, or 3 heteroatom(s) mutually independently selected from the group consisting of oxygen, sulfur and nitrogen (NH) as ring member(s). A heterocycloalkenyl residue may be unsubstituted or monosubstituted or identically or differently polysubstituted. In one or more embodiments, heterocycloalkenyl residues may be 4 to 9-membered, specifically 4- to 7-membered, very specifically 5- to 7-membered.

Examples which may be mentioned of suitable heterocycloalkenyl residues or of suitable 5 to 7-membered heterocycloalkenyl residues which may be unsubstituted or mono- or polysubstituted are (2,3)-dihydrofuranyl, (2,5)-di-hydrofuranyl, (2,3)-dihydrothienyl, (2,5)-dihydrothienyl, (2,3)-dihydropyrrolyl, (2,5)-dihydropyrrolyl, (2,3)-dihydroisoxazolyl, (4,5)-dihydroisoxazolyl, (2,5)-dihydroisothiazolyl, (2,3)-dihydropyrazolyl, (4,5)-dihydropyrazolyl, (2,5)-dihydropyrazolyl, (2,3)-dihydrooxazolyl, (4,5)-dihydrooxazolyl, (2,5)-dihydrooxazolyl, (2,3)-dihydrothiazolyl, (4,5)-dihydrothiazolyl, (2,5)-dihydrothiazolyl, (2,3)-dihydroimidazolyl, (4,5)-dihydroimidazolyl, (2,5)-dihydroimidazolyl, (3,4,5,6)-tetrahydropyridin-2-yl, (1,2,5,6)-tetrahydropyridin-1-yl, (1, 2)-dihydropyridin-1-yl, (1,4)-dihydropyridin-1-yl, dihydropyranyl, and (1, 2, 3, 4)-tetrahydropyridin-1-yl.

The cycloalkyl residues, heterocycloalkyl residues, cycloalkenyl residues or heterocycloalkenyl residues may for the purposes of the present invention be fused (anellated) with an unsubstituted or at least monosubstituted mono- or bicyclic ring system. For the purposes of the present invention, a mono- or bicyclic ring system should be understood to mean monoor bicyclic hydrocarbon residues which may be saturated, unsaturated or aromatic and optionally comprise one or more heteroatoms as ring members. In one or more embodiments, the rings of the above-stated mono- or bicyclic ring systems are in each case 4-, 5-, or 6-membered and may in each case optionally comprise 0, 1, 2, 3, 4, or 5 heteroatom(s), specifically optionally 0, 1, or 2 heteroatom(s) as ring member(s), which are mutually independently selected from the group consisting of oxygen, nitrogen and sulfur. If a bicyclic ring system is present, the different rings may, in each case mutually independently, exhibit a different degree of saturation, i.e. be saturated, unsaturated or aromatic.

Examples which may be mentioned of suitable cycloalkyl residues, heterocycloalkyl residues, cycloalkenyl residues or heterocyclalkenyl residues which may be unsubstituted or mono- or polysubstituted, and are fused with a mono- or bicyclic ring system, are (1,2,3,4)-tetrahydroquinolinyl, (1,2,3,4)-tetrahydroisoquinolinyl, (2, 3)-dihydro-1H-isoindolyl, (1,2,3,4)-tetrahydronaphthyl, (2,3)-dihydrobenzo[1.4]dioxinyl, benzo[1.3]dioxolyl, (3,4)-dihydro-2H-benzo[1.4]oxazinyl and octahydro-pyrrolo[3,4-c]pyrrolyl.

If one or more of the substituents denote any cycloalkyl residue, cycloalkenyl residue, heterocycloalkyl residue or heterocycloalkenyl residues which is at least monosubstituted, this may be substituted with optionally 1, 2, 3, 4, or 5, specifically with optionally 1, 2, or 3, substituents mutually independently selected from the group consisting of F, Cl, Br, I, —CN, —NO$_2$, —OH, —SH, —NH$_2$, —C(=O)—OH, —C$_{1-5}$ alkyl, —(CH$_2$)—O—C$_{1-5}$-alkyl, —C$_{2-5}$ alkenyl, —C$_{2-5}$ alkynyl, —C≡C—Si(CH$_3$)$_3$, —C≡C—Si(C$_2$H$_5$)$_3$, —S—$C_{1-5}$-alkyl, —S-phenyl, —S—$CH_2$-phenyl, —O—$C_{1-5}$-alkyl, —O-phenyl, —O—$CH_2$-phenyl, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —S(=O)$_2$-phenyl, —S(=O)$_2$—$C_{1-5}$-alkyl, —S(=O)—$C_{1-5}$-alkyl, —NH—$C_{1-5}$-alkyl, N($C_{1-5}$alkyl)$_2$, —C(=O)—O—$C_{1-5}$-alkyl, —C(=O)—H; —C(=O)—$C_{1-5}$-alkyl, —$CH_2$—O—C(=O)-phenyl, —O—C(=O)-phenyl, —NH—S(=O)$_2$—$C_{1-5}$-alkyl, —NH—C(=O)—$C_{1-5}$-alkyl, —C(=O)—$NH_2$, —C(=O)—NH—$C_{1-5}$-alkyl, —C(=O)—N($C_{1-5}$-alkyl)$_2$, pyrazolyl, phenyl, furyl (furanyl), thiazolyl, thiadiazolyl, thiophenyl (thienyl), benzyl and phenethyl, wherein the above-stated $C_{1-5}$ alkyl residues may in each case be linear or branched and the cyclic substituents or the cyclic residues of these substituents themselves may be substituted with optionally 1, 2, 3, 4, or 5, specifically with optionally 1, 2, 3, or 4, substituents mutually independently selected from the group consisting of F, Cl, Br, I, —CN, —$NO_2$, —OH, —SH, —$NH_2$, —C(=O)—OH, —$C_{1-5}$ alkyl, —($CH_2$)—O—$C_{1-5}$-alkyl, —$C_{2-5}$ alkenyl, —$C_{2-5}$ alkynyl, —C≡C—Si($CH_3$)$_3$, —C≡C—Si($C_2H_5$)$_3$, —S—$C_{1-5}$-alkyl, —S-phenyl, —S—$CH_2$-phenyl, —O—$C_{1-5}$-alkyl, —O-phenyl, —O—$CH_2$-phenyl, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$ and —S—$CH_2F$.

In one or more embodiments, the substituents may be in each case mutually independently selected from the group consisting of F, Cl, Br, I, —CN, —$NO_2$, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si($CH_3$)$_3$, —C≡C—Si($C_2H_5$)$_3$, —$CH_2$—O—$CH_3$, —$CH_2$—O—$C_2H_5$, —OH, —SH, —$NH_2$, —C(=O)—OH, —S—$CH_3$, —S—$C_2H_5$, —S(=O)—$CH_3$, —S(=O)$_2$—$CH_3$, —S(=O)—$C_2H_5$, —S(=O)$_2$—$C_2H_5$, —O—$CH_3$, —O—$C_2H_5$, —O—$C_3H_7$, —O—C($CH_3$)$_3$, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —S(=O)$_2$-phenyl, pyrazolyl, phenyl, —N($CH_3$)$_2$, —N($C_2H_5$)$_2$, —NH—$CH_3$, —NH—$C_2H_5$, —$CH_2$—O—C(=O)-phenyl, —NH—S(=O)$_2$—$CH_3$, —C(=O)—O—$CH_3$, —C(=O)—O—$C_2H_5$, —C(=O)—O—C($CH_3$)$_3$, —C(=O)—H, —C(=O)—$CH_3$, —C(=O)—$C_2H_5$, —NH—C(=O)—$CH_3$, —NH—C(=O)—$C_2H_5$, —O—C(=O)-phenyl, —C(=O)—$NH_2$, —C(=O)—NH—$CH_3$, —C(=O)—N($CH_3$)$_2$, phenyl, furyl (furanyl), thiadiazolyl, thiophenyl (thienyl) and benzyl, wherein the cyclic substituents or the cyclic residues of these substituents themselves may in each case be substituted with optionally 1, 2, 3, 4, or 5, specifically with optionally 1, 2, 3, or 4, substituents mutually independently selected from the group consisting of F, Cl, Br, I, —CN, —$NO_2$, —OH, —SH, —$NH_2$, —C(=O)—OH, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si($CH_3$)$_3$, —C≡C—Si($C_2H_5$)$_3$, —$CH_2$—O—$CH_3$, —$CH_2$—O—$C_2H_5$, —S—$CH_3$, —S—$C_2H_5$, —S(=O)—$CH_3$, —S(=O)$_2$—$CH_3$, —S(=O)—$C_2H_5$, —S(=O)$_2$—$C_2H_5$, —O—$CH_3$, —O—$C_2H_5$, —O—$C_3H_7$, —O—C($CH_3$)$_3$, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, and —S—$CH_2F$.

The term "aryl" means in the sense of this invention aromatic hydrocarbons having up to 14 ring members, including phenyls and naphthyls. Each aryl residue can be unsubstituted or mono- or polysubstituted, wherein the aryl substituents can be the same or different and in any desired and possible position of the aryl. The aryl can be bound to the superordinate general structure via any desired and possible ring member of the aryl residue. The aryl residues can also be condensed with further saturated, (partially) unsaturated, (hetero)cyclic, aromatic or heteroaromatic ring systems, i.e. with cycloalkyl, heterocyclyl, aryl, or heteroaryl which can in turn be unsubstituted or mono- or polysubstituted. Examples of condensed aryl residues are benzodioxolanyl and benzodioxanyl. In one or more embodiments, aryl is selected from the group containing phenyl, 1-naphthyl and 2-naphthyl which can be respectively unsubstituted or mono- or polysubstituted. In one or more specific embodiments, aryl is phenyl, unsubstituted or mono- or polysubstituted.

In relation to "aryl", the term "mono- or polysubstituted" refers in the sense of this invention to the single or multiple, for example double, triple or quadruple, substitution of one or more hydrogen atoms of the ring system each independently of one another by substituents selected from the group consisting of F, Cl, Br, I, —CN, —$NO_2$, —OH, —SH, —$NH_2$, —C(=O)—OH, —$C_{1-5}$ alkyl, —($CH_2$)—O—$C_{1-5}$-alkyl, —$C_{2-5}$ alkenyl, —$C_{2-5}$ alkynyl, —C≡C—Si($CH_3$)$_3$, —C≡C—Si($C_2H_5$)$_3$, —S—$C_{1-5}$-alkyl, —S-phenyl, —S—$CH_2$-phenyl, —O—$C_{1-5}$-alkyl, —O-phenyl, —O—$CH_2$-phenyl, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —S(=O)$_2$-phenyl, —S(=O)$_2$—$C_{1-5}$-alkyl, —S(=O)—$C_{1-5}$-alkyl, —NH—$C_{1-5}$-alkyl, N($C_{1-5}$alkyl)$_2$, —C(=O)—O—$C_{1-5}$-alkyl, —C(=O)—H; C(=O)—$C_{1-5}$-alkyl, —$CH_2$—O—C(=O)-phenyl, —O—C(=O)-phenyl, —NH—S(=O)$_2$—$C_{1-5}$-alkyl, —NH—C(=O)—$C_{1-5}$-alkyl, —C(=O)—$NH_2$, —C(=O)—NH—$C_{1-5}$-alkyl, —C(=O)—N($C_{1-5}$-alkyl)$_2$, pyrazolyl, phenyl, furyl (furanyl), thiazolyl, thiadiazolyl, thiophenyl (thienyl), benzyl, and phenethyl, wherein the above-stated $C_{1-5}$ alkyl residues may in each case be linear or branched and the cyclic substituents or the cyclic residues of these substituents themselves may be substituted with optionally 1, 2, 3, 4, or 5, specifically with optionally 1, 2, 3, or 4, substituents mutually independently selected from the group consisting of F, Cl, Br, I, —CN, —$NO_2$, —OH, —SH, —$NH_2$, —C(=O)—OH, —$C_{1-5}$ alkyl, —($CH_2$)—O—$C_{1-5}$-alkyl, —$C_{2-5}$ alkenyl, —$C_{2-5}$alkynyl, —C≡C—Si($CH_3$)$_3$, —C≡C—Si($C_2H_5$)$_3$, —S—$C_{1-5}$-alkyl, —S-phenyl, —S—$CH_2$-phenyl, —O—$C_{1-5}$-alkyl, —O-phenyl, —O—$CH_2$-phenyl, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, and —S—$CH_2F$.

In one or more embodiments, the substituents may be in each case mutually independently selected from the group consisting of F, Cl, Br, I, —CN, —$NO_2$, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si($CH_3$)$_3$, —C≡C—Si($C_2H_5$)$_3$, —$CH_2$—O—$CH_3$, —$CH_2$—O—$C_2H_5$, —OH, —SH, —$NH_2$, —C(=O)—OH, —S—$CH_3$, —S—$C_2H_5$, —S(=O)—$CH_3$, —S(=O)$_2$—$CH_3$, —S(=O)—$C_2H_5$, —S(=O)$_2$—$C_2H_5$, —O—$CH_3$, —O—$C_2H_5$, —O—$C_3H_7$, —O—C($CH_3$)$_3$, —$CF_3$, —$CHF_2$, —$CH_2F$, —O—$CF_3$, —O—$CHF_2$, —O—$CH_2F$, —C(=O)—$CF_3$, —S—$CF_3$, —S—$CHF_2$, —S—$CH_2F$, —S(=O)$_2$-phenyl, pyrazolyl, phenyl, —N($CH_3$)$_2$, —N($C_2H_5$)$_2$, —NH—$CH_3$, —NH—$C_2H_5$, —$CH_2$—O—C(=O)-phenyl, —NH—S(=O)$_2$—$CH_3$, —C(=O)—O—$CH_3$, —C(=O)—O—$C_2H_5$, —C(=O)—O—C($CH_3$)$_3$, —C(=O)—H, —C(=O)—$CH_3$, —C(=O)—$C_2H_5$, —NH—C(=O)—$CH_3$, —NH—C(=O)—$C_2H_5$, —O—C(=O)-phenyl, —C(=O)—$NH_2$, —C(=O)—NH—$CH_3$, —C(=O)—N($CH_3$)$_2$, phenyl, furyl (furanyl), thiadiazolyl, thiophenyl (thienyl), and benzyl, wherein the cyclic substituents or the cyclic residues of these substituents themselves may in each case be substituted with optionally 1, 2, 3, 4, or 5, specifically with optionally 1, 2, 3, or 4, substituents mutually independently selected from the group consisting of F, Cl, Br, I, —CN, —NO$_2$, —OH, —SH, —NH$_2$, —C(=O)—OH, methyl, ethyl, n-propyl, isopropyl, n-butyl, isobutyl, 2-butyl, tert.-butyl, n-pentyl, neopentyl, ethenyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, and —S—CH$_2$F.

In one or more embodiments, R$^5$ denotes unsubstituted C$_{1-5}$ alkyl. In specific embodiments, R$^5$ denotes a moiety selected from the group consisting of methyl, ethyl and iso-propyl.

In one or more embodiments, R$^1$ and R$^3$, mutually independently, in each case denote H; F; Cl; Br; I; unsubstituted or at least monosubstituted C$_{1-12}$ alkyl; unsubstituted or at least monosubstituted C$_{3-8}$ cycloalkyl; or unsubstituted or mono- or polysubstituted aryl; and R$^2$ and R$^4$, in each case denote H.

In one or more specific embodiments, R$^1$ and R$^3$, mutually independently, in each case denote a moiety selected from the group consisting of methyl, ethyl, propyl, isopropyl, n-butyl, isobutyl, tert-butyl, n-pentyl, 1,1-dimethylpropyl, 2,2-dimethylpropyl, 3-methylbutyl, hexyl, 2-ethylhexyl, heptyl, octyl, nonyl, decyl, undecyl, dodecyl, cyclopentyl, cyclohexyl, 1,1,3,3,-tetramethylbutyl, sec-butyl, CH$_3$—CH$_2$—C(CH$_3$)$_2$— and unsubstituted phenyl; and R$^2$ and R$^4$, in each case denote H.

In one or more embodiments, the at least one Lewis acid is a metal-containing compound selected from the group consisting of a) AsX$_3$, GaX$_3$, BX$_3$, BX$_3$.(C$_2$H$_5$)$_2$O, BX$_3$.S(CH$_3$)$_2$, AlX$_3$, (C$_2$H$_5$)$_2$AlX, SbX$_3$, SbX$_5$, SnX$_2$, MgX$_2$, MgX$_2$.O(C$_2$H$_5$)$_2$, ZnX$_2$, BiX$_3$, FeX$_2$, TiX$_2$, TiX$_4$, NbX$_5$, NiX$_2$, CoX$_2$, HgX$_2$, whereby X in each case denotes F, Cl, Br, or I, b) BH$_3$, B(CH$_3$)$_3$, GaH$_3$, AlH$_3$, Al(acetate)(OH)$_2$, Al[OCH(CH$_3$)$_2$]$_3$, Al(OCH$_3$)$_3$, Al(OC$_2$H$_5$), Al$_2$O$_3$, (CH$_3$)$_3$Al, Ti[OCH(CH$_3$)$_2$]$_3$Cl, Ti[OCH(CH$_3$)$_2$]$_4$, methylaluminum di-(2,6-di-tert-butyl-4-methylphenoxide), methylaluminum di-(4-brom-2,6-di-tert-butylphenoxide), LiClO$_4$, c) Mg(acetate)$_2$, Zn(acetate)$_2$, Ni(acetate)$_2$, Ni(NO$_3$)$_2$, Co(acetate)$_2$, Co(NO$_3$)$_2$, Cu(acetate)$_2$, Cu(NO$_3$)$_2$, Li(acetate), Zr(acetylacetonate)$_4$, Si(acetate)$_4$, K(acetate), Na(acetate), Cs(acetate), Rb(acetate), Mn(acetate)$_2$, Fe(acetate)$_2$, Bi(acetate)$_3$, Sb(acetate)$_3$, Sr(acetate)$_2$, Sn(acetate)$_2$, Zr(acetate)$_2$, Ba(acetate)$_2$, Hg(acetate)$_2$, Ag(acetate), Tl(acetate)$_3$, d) Sc(fluoromethansulfonate)$_3$, Ln(fluoromethanesulfonate)$_3$, Ni(fluoromethanesulfonate)$_2$, Ni(tosylate)$_2$, Co(fluoromethanesulfonate)$_2$, Co(tosylate)$_2$, Cu(fluoromethanesulfonate)$_2$ and Cu(tosylate)$_2$.

In one or more embodiments, the at least one Lewis acid is a metal-containing compound selected from the group consisting of a) AsF$_3$, AsCl$_3$, AsBr$_3$, AsI$_3$, GaF$_3$, GaCl$_3$, GaBr$_3$, GaI$_a$, BF$_3$, BCl$_3$, BBr$_3$, BI$_3$, BF$_3$.(C$_2$H$_5$)$_2$O, BCl$_3$.(C$_2$H$_5$)$_2$O, BBr$_3$.(C$_2$H$_5$)$_2$O, BI$_3$.(C$_2$H$_5$)$_2$O, BF$_3$.S(CH$_3$)$_2$, BCl$_3$.S(CH$_3$)$_2$, BBr$_3$.S(CH$_3$)$_2$, BI$_3$S(CH$_3$)$_2$, AlF$_3$, AlCl$_3$, AlBr$_3$, AlI$_3$, (C$_2$H$_5$)$_2$AlCl, SbF$_3$, SbCl$_3$, SbBr$_3$, SbI$_3$, SbF$_5$, SbCl$_5$, SbBr$_5$, SbI$_5$, SnF$_2$, SnCl$_2$, SnBr$_2$, SnI$_2$, MgF$_2$, MgCl$_2$, MgBr$_2$, MgI$_2$, MgF$_2$.O(C$_2$H$_5$)$_2$, MgCl$_2$.O(C$_2$H$_5$)$_2$, MgBr$_2$.O(C$_2$H$_5$)$_2$, MgI$_2$.O(C$_2$H$_5$)$_2$, ZnF$_2$, ZnCl$_2$, ZnBr$_2$, ZnI$_2$, BiF$_3$, BiCl$_3$, BiBr$_3$, BiI$_3$, FeF$_2$, FeCl$_2$, FeBr$_2$, FeI$_2$, TiF$_2$, TiCl$_2$, TiBr$_2$, TiI$_2$, TiF$_4$, TiCl$_4$, TiBr$_4$, TiI$_4$, NbF$_5$, NbCl$_5$, NbBr$_5$, NbI$_5$, NiF$_2$, NiCl$_2$, NiBr$_2$, NiI$_2$, CoF$_2$, CoCl$_2$, CoBr$_2$, CoI$_2$, b) Al[OCH(CH$_3$)$_2$]$_3$, Al(OCH$_3$)$_3$, Al(OC$_2$H$_5$), Al$_2$O$_3$, (CH$_3$)$_3$Al, Ti[OCH(CH$_3$)$_2$]$_3$Cl, Ti[OCH(CH$_3$)$_2$]$_4$, methylaluminum di-(2,6-di-tert-butyl-4-methylphenoxide), methylaluminum di-(4-brom-2,6-di-tert-butylphenoxide), LiClO$_4$, c) Mg(acetate)$_2$, Zn(acetate)$_2$, Ni(acetate)$_2$, Ni(NO$_3$)$_2$, Co(acetate)$_2$, Co(NO$_3$)$_2$, Cu(acetate)$_2$, Cu(NO$_3$)$_2$, d) Sc(fluoromethansulfonate)$_3$, Ln(fluoromethanesulfonate)$_3$, Ni(fluoromethanesulfonate)$_2$, Ni(tosylate)$_2$, Co(fluoromethanesulfonate)$_2$, Co(tosylate)$_2$, Cu(fluoromethanesulfonate)$_2$ and Cu(tosylate)$_2$.

In one or more specific embodiments, the at least one Lewis acid is a metal-containing compound selected from the group consisting of AlX$_3$, SnX$_2$, MgX$_2$, MgX$_2$.O(C$_2$H$_5$)$_2$, ZnX$_2$, BiX$_3$, FeX$_2$, Al[OCH(CH$_3$)$_2$]$_3$, Al(OCH$_3$)$_3$, and Al(OC$_2$H$_5$)$_3$, whereby X in each case denotes F, Cl, Br or I.

In other specific embodiments, the at least one Lewis acid is a metal-containing compound selected from the group consisting of AlCl$_3$, SnCl$_2$, MgCl$_2$, MgCl$_2$.O(C$_2$H$_5$)$_2$, ZnCl$_2$, BiCl$_3$, FeCl$_2$, Al[OCH(CH$_3$)$_2$]$_3$, Al(OCH$_3$)$_3$, and Al(OC$_2$H$_5$)$_3$.

In a further embodiment, mixtures of different Lewis acids can be used.

In a specific embodiment, the presently claimed invention relates to a process for the preparation of a compound of general formula (I)

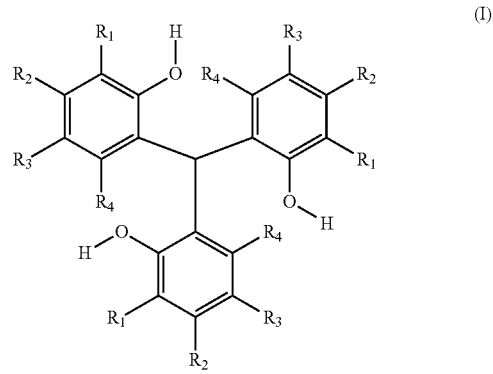

wherein R$^1$ and R$^3$, mutually independently, in each case denote a moiety selected from the group consisting of methyl, ethyl, propyl, isopropyl, n-butyl, isobutyl, tert-butyl, n-pentyl, 1,1-dimethylpropyl, 2,2-dimethylpropyl, 3-methylbutyl, hexyl, 2-ethylhexyl, heptyl, octyl, nonyl, decyl, undecyl, dodecyl, cyclopentyl, cyclohexyl, sec-butyl, CH$_3$—CH$_2$—C(CH$_3$)$_2$—, 1,1,3,3,-tetramethylbutyl, and unsubstituted phenyl; and R$^2$ and R$^4$, in each case denote H;

comprising at least the step of reacting at least one compound of general formula (II)

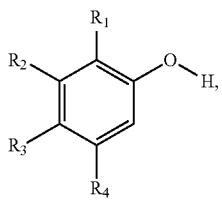

(II)

wherein $R^1$ and $R^3$, mutually independently, in each case denote a moiety selected from the group consisting of methyl, ethyl, propyl, isopropyl, n-butyl, isobutyl, tert-butyl, n-pentyl, 1,1-dimethylpropyl, 2,2-dimethylpropyl, 3-methylbutyl, hexyl, 2-ethylhexyl, heptyl, octyl, nonyl, decyl, undecyl, dodecyl, cyclopentyl, cyclohexyl, 1,1,3,3,-tetramethylbutyl, sec-butyl, $CH_3$—$CH_2$—$C(CH_3)_2$—, and unsubstituted phenyl; and $R^2$ and $R^4$, in each case denote H;
with at least one compound of general formula (III)

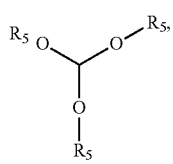

(III)

wherein $R^5$ in each case denotes a moiety selected from the group consisting of methyl, ethyl and iso-propyl;
in the presence of at least one metal-containing compound selected from the group consisting of $AlCl_3$, $SnCl_2$, $MgCl_2$, $ZnCl_2$, $BiCl_3$, $FeCl_2$, $Al[OCH(CH_3)_2]_3$, $Al(OCH_3)_3$, and $Al(OC_2H_5)_3$.

In one or more embodiments, the molar ratio of the at least one compound of general formula (II) to the at least one compound of general formula (III) is in in the range of 5.0:1.0 and 2.5:1.0, more specifically the molar ratio of the at least one compound of general formula (II) to the at least one compound of general formula (III) is in in the range of 3.0:1.0 and 2.6:1.0.

In one or more embodiments, the concentration of the at least one metal-containing compound in relation to the at least one compound of general formula (II) is in in the range of 1 mol-% to 60 mol-%, more specifically in the range of 5 mol-% to 50 mol-%, most specifically in the range of 30 mol-% to 50 mol-%. The at least one metal-containing compound is added to the mixture containing at least one compound of general formula (II) and the at least one compound of general formula (III) in one portion or in several portions such as 2, 3 or 4 portions.

In one or more embodiments, the at least one compound of general formula (II) and the at least one compound of general formula (III) are reacted in at least one inert organic solvent having a boiling point in the range of 80° C. to 185° C. More specifically, the at least one compound of general formula (II) and the at least one compound of general formula (III) are reacted in at least one inert organic solvent selected from the group consisting of toluene, xylene, orthoxylene, para-xylene, mesitylene, cyclohexane, cyclopentanone, benzonitrile, chlorobenzene, 1,2-dichlorobenzene, 1,2-dichloroethane, dibutylether, anisol, butylacetate, methylethylketone, methylisobutylketone, pinacolone, dimethylformamide, and acetonitrile, most specifically the at least one compound of general formula (II) and the at least one compound of general formula (III) are reacted in at least one inert organic solvent selected from the group consisting of toluene, xylene, mesitylene, and cyclohexane. The aforementioned inert organic solvents can also be used as mixtures of different solvents.

In an alternative embodiment, the reaction of the at least one compound of general formula (II) and the at least one compound of general formula (III) does not require the addition of organic solvents. In case the reaction of the at least one compound of general formula (II) and the at least one compound of general formula (III) is carried out without any additional solvent, the at least one compound of general formula (II) is used at a molar concentration in the range of 1.0 M to 8.0 M, more specifically at a molar concentration in the range of 3.0 M to 8.0 M.

In one or more embodiments, the at least one compound of general formula (II) and the at least one compound of general formula (III) are reacted in an inert solvent, whereby the molar concentration of the at least one compound of general formula (II) is in the range of 1.0 M to 8.0 M, more specifically at a molar concentration in the range of 3.0 M to 8.0 M, most specifically at a molar concentration in the range of 5.0 M to 8.0 M.

The time for fully converting the at least one compound of general formula (II) to the at least one compound of general formula (I) depends on the amount of catalyst that is used and the reaction temperature. However, in one or more embodiments, the at least one compound of general formula (II) and the at least one compound of general formula (III) are reacted at a temperature in the range of 70° C. to 140° C. for a period in the range of 2 to 20 hours, more specifically at a temperature in the range of 85° C. to 105° C. for a period in the range of 3 to 20 hours.

The at least one compound of general formula (I) can be isolated and purified by a variety of different methods. However, in one aspect of the presently claimed invention the at least one compound of general formula (I) is purified and isolated by applying the following steps:
(a) adding an inert organic solvent and water;
(b) separating the organic phase from the water phase;
(c) optionally washing the organic phase with a 1N aqueous solution of hydrochloric acid;
(d) washing the organic phase with water;
(e) filtering the organic phase and drying of the thus obtained residue to obtain the at least one compound of general formula (I).

In another aspect, the presently claimed invention is directed to the use of a compound that is obtained by the inventively claimed process for enhanced oil recovery.

EXAMPLES

Preparation of 2-(bis(2-hydroxy-3,5-di-tert-butylphenyl)methyl)-4,6-di-tert-butylphenol (Example 1)
[CAS No. 143560-44-5]

2,4-di-tert.-Butylphenol was melted in an oven at 80° C. 41.6 g (200 mmol) of melted 2,4-di-tert.-butylphenol was directly weighted into a 250 mL-flask. 30 mL toluene (abs.) was added and under stifling the mixture was heated up to 50° C. until a clear solution was obtained. The concentration of 2,4-di-tert.-butylphenol in toluene was 6.66 M. 12.3 mL (73 mmol) Triethylorthoformiate were added and a clear solution was then obtained. 8 g (80 mmol) Magnesium chloride (salt A) was added. A white suspension was obtained. The reaction mixture was heated up to 100° C., a nearly green solution was obtained. After 8 hours at 100° C. a brown suspension formed.

The reaction was cooled down to about 60° C. 50 mL toluene (technical grade) were added, the reaction mixture was stirred for 10 min. The suspension was cooled down to about 25° C. 50 mL of deionized water was added. The temperature rose to 33° C. The reaction mixture was left under stirring for 10 min. After stopping the stirrer, 2 phases were rapidly obtained: the solid remained suspended in the organic phase. The separation of the phases was done in a 500 mL separatory funnel. A clear water phase with a pH of about 10 was obtained. The organic phase was washed successively with: (i) 50 mL water with 0.2 mL 1N HCL solution; a pH of 5 was obtained, the extraction was followed by a rapid separation, the aqueous phase was separated and (ii) 50 mL water; a pH of 6 was obtained, the extraction was followed by a rapid separation, the aqueous phase was separated. The solid was dispersed in the organic phase.

The organic phase containing the suspended solid was filtered over a Buchner funnel. The filter cake was washed twice with little toluene (in total about 50 mL). The drying of the filter cake was done in the vacuum oven at 80° C. until constant weight. The desired product was obtained as a white solid (27.7 g, 66% of theory).

The above-identified procedure was carried out with additional salts at different conditions (table 1).

Preparation of 2-[bis[3,5-bis(1,1-dimethylpropyl)-2-hydroxy-phenyl]methyl]-4,6-bis(1,1-dimethylpropyl) phenol (Example 27)

197 g (800 mmol) of 2,4-di-tert-amylphenol was solubilized in 120 mL toluene in a 1.5 L-flask. 32 g (320 mmol) magnesium chloride was added. 50 mL (292 mmol) Triethylorthoformiate was added to the resulting suspension. The reaction mixture was heated to 100° C., a green solution was obtained. After 20 hours at 100° C. a yellow suspension formed.

The reaction mixture was cooled down to about 20° C. 200 mL toluene and 200 mL ethyl acetate were added. The organic phase was washed 3 times with 200 mL deionized water. The solvent was eliminated by distillation. 250 mL ethanol was added to the crude and stirred at 40° C. The resulting suspension was cooled down to 0° C., filtered over a funnel. The filter cake was washed with cold ethanol and dried in the vacuum oven at 80° C. until constant weight. The desired product was obtained as a white solid (94 mg, 51% of theory).

Preparation of 2-[bis(5-tert-butyl-2-hydroxy-3-sec-butyl-phenyl)methyl]-4-tert-butyl-6-sec-butyl-phenol (Example 28)

173 g 2-secbutyl-4-tert-butylphenol (800 mmol) was solubilized in 120 mL toluene in a 1.5 L-flask. 32 g (320 mmol) magnesium chloride was added. 50 mL (292 mmol) Triethylorthoformiate was added to the resulting suspension. The reaction mixture was heated to 100° C., a green solution was obtained. After 20 hours at 100° C. a yellow suspension

TABLE 1

| Example | Salt | Concentration of Phenol [M] | Concentration of the salt based on phenol [mol.-%] | Excess of triethylorthoformiate [mol.-%] | Solvent | Reaction time [h] and temperature [° C.] | Yield [%] |
|---|---|---|---|---|---|---|---|
| 2 | $AlCl_3$ | 3.33 | 5 | 10 | Toluene | 17/100 | 14 |
| 3 | $SnCl_2$ | 3.33 | 5 | 10 | Toluene | 17/100 | 35 |
| 4 | $MgCl_2$ | 3.33 | 5 | 10 | Toluene | 17/100 | 45 |
| 5 | $ZnCl_2$ | 3.33 | 5 | 10 | Toluene | 17/100 | 48 |
| 6 | $BiCl_3$ | 3.33 | 5 | 10 | Toluene | 17/100 | <10 |
| 7 | $FeCl_2$ | 3.33 | 5 | 10 | Toluene | 17/100 | 24 |
| 8 | $Al[OCH(CH_3)_2]_3$ | 3.33 | 5 + 5 | 10 | Toluene | 17/100 | 31 |
| 9 | $Al[OCH(CH_3)_2]_3$ | 3.33 | 20 | 10 | Toluene | 17/100 | 25 |
| 10 | $Al[OCH(CH_3)_2]_3$ | 3.33 | 40 | 10 | Toluene | 17/100 | 31 |
| 11 | $MgCl_2$ | 3.33 | 1 | 10 | Toluene | 17/100 | 25 |
| 12 | $MgCl_2$ | 3.33 | 2.5 | 10 | Toluene | 17/100 | 27 |
| 13 | $MgCl_2$ | 3.33 | 5 | 10 | Toluene | 17/100 | 45 |
| 14 | $MgCl_2$ | 6.67 | 50 | 10 | Butyl acetate | 6/100 | 35 |
| 15 | $MgCl_2$ | 6.67 | 50 | 10 | Xylene | 6/100 | 70 |
| 16 | $MgCl_2$ | 6.67 | 50 | 10 | Mesitylene | 6/100 | 69 |
| 17 | $MgCl_2$ | 6.67 | 50 | 10 | Cyclohexane | 20/85 | 75 |
| 18 | $MgCl_2$ | 6.67 | 50 | 10 | Chlorobenzene | 6/100 | 64 |
| 19 | $MgCl_2$ | 6.67 | 50 | 10 | 1,2-Dichlorobenzene | 6/100 | 72 |
| 20 | $MgCl_2$ | 6.67 | 50 | 10 | 1,2-Dichloroethane | 20/85 | 74 |
| 21 | $MgCl_2$ | 6.67 | 50 | 10 | Dibutyl-ether | 6/100 | 63 |
| 22 | $MgCl_2$ | 6.67 | 50 | 10 | Anisol | 6/100 | 67 |
| 23 | $MgCl_2$ | 6.67 | 50 | 10 | Butyl acetate | 6/100 | 69 |
| 24 | $MgCl_2$ | 6.67 | 50 | 10 | Methyl ethylketone | 20/85 | 18 |
| 25 | $MgCl_2$ | 6.67 | 50 | 10 | DMF | 6/100 | 29 |
| 26 | $MgCl_2$ | 6.67 | 50 | 10 | Acetonitrile | 20/85 | 62 | formed. The reaction mixture was cooled down. 300 mL toluene and 300 mL ethyl acetate were added. The organic phase was washed 3 times with 200 mL deionized water. The solvent was eliminated by distillation. 200 mL hexane was added to the crude, the resulting suspension was filtered over a funnel. The filter cake was washed with hexane and dried in the vacuum oven at 80° C. until constant weight. The desired product was obtained as a white solid. (82 g, 49% of theory). Additional product (15.1 g, 9% of theory) was obtained from the mother liquor after elimination of the solvent and crystallization in hexane, filtration, washing with hexane and subsequent drying.

Preparation of 2-[bis(5-tert-butyl-2-hydroxy-3-isopropyl-phenyl)methyl]-4-tert-butyl-6-isopropyl-phenol (Example 29)

176 g (800 mmol) 4-tert-butyl-2-isopropylphenol was solubilized in 120 ml toluene in a 1.5 L-flask. 32 g (320 mmol) magnesium chloride was added. 50 mL (292 mmol) Triethylorthoformiate was added to the resulting suspension. The reaction mixture was heated to 100° C., a green solution was obtained. After 20 hours at 100° C. a brown suspension formed.

The reaction mixture was cooled down. 400 mL toluene was added. The organic phase was washed 3 times with 200 mL deionized water. The solvent was eliminated by distillation. 200 mL hexane were added to the crude, the resulting suspension was filtered over a funnel. The filtercake was washed with hexane and dried in the vacuum oven at 80° C. until constant weight. The desired product was obtained as a white solid. (46.6 g, 30% of theory). Additional product (34.4 g, 22% of theory) was obtained from the mother liquor after elimination of the solvent and crystallization in hexane, filtration, washing with hexane and subsequent drying.

Preparation of 2-[bis(2-hydroxy-3,5-diphenyl-phenyl)methyl]-4,6-diphenyl-phenol (Example 30)

200 g (800 mmol) 2,4-diphenylphenol was suspended in 120 mL toluene in a 1.5 L-flask. 32 g (320 mmol) magnesium chloride was added. 50 mL (292 mmol) Triethylorthoformiate was added to the suspension. The reaction mixture was heated to 100° C., after 30 min the thick suspension was diluted with additional 200 mL toluene, after 2 hours again 100 mL toluene was added. After 8 hours at 100° C. a fine yellow suspension formed.

The reaction mixture was cooled down. 200 mL water was added followed by addition of 250 mL ethylacetate. The organic phase, a suspension, was washed 3 times with 200 mL deionized water. The suspension was filtered over a funnel. The filter cake was washed with ethylacetate and dried in the vacuum oven at 80° C. until constant weight. The desired product was obtained as a white solid. (72.9 g 37% of theory).

What is claimed is:
1. A process for the preparation of a compound of general formula (I)

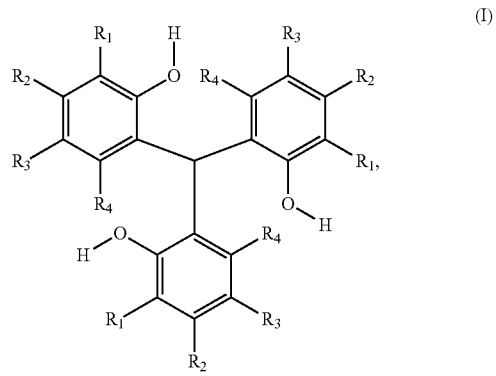

wherein $R^1$, $R^2$, $R^3$ and $R^4$, mutually independently, in each case denote H; F; Cl; Br; I; —OH; —NO$_2$; —CN; —C(=O)—R$^6$; —C(=O)—O—R$^7$; —O—C(=O)—R$^8$; —NH—C(=O)—R$^9$; —C(=O)—NH$_2$; —C(=O)—NH—R$^{10}$; —C(=O)—NR$^{11}$R$^{12}$; —O—R$^{13}$; —S—R$^{14}$; —S(=O)—R$^{15}$; —S(=O)$_2$—R$^{16}$; (unsubstituted or at least monosubstituted alkyl; unsubstituted or at least monosubstituted heteroalkyl; unsubstituted or at least monosubstituted cycloalkyl; unsubstituted or at least monosubstituted cycloalkenyl; unsubstituted or at least monosubstituted heterocycloalkyl; unsubstituted or at least monosubstituted heterocycloalkenyl or unsubstituted or mono- or polysubstituted aryl;

and $R^6$, $R^7$, $R^8$, $R^9$, $R^{10}$, $R^{11}$, $R^{12}$, $R^{13}$, $R^{14}$, $R^{15}$ and $R^{16}$, mutually independently, in each case denote unsubstituted or at least monosubstituted alkyl; unsubstituted or at least monosubstituted alkenyl or unsubstituted or at least monosubstituted heteroalkyl;

the process comprising at least the step of reacting at least one compound of general formula (II)

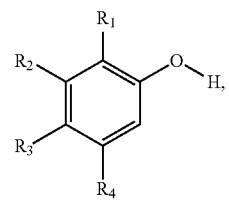

wherein $R^1$, $R^2$, $R^3$ and $R^4$, mutually independently, in each case denote H; F; Cl; Br; I; —OH; —NO$_2$; —CN; —C(=O)—R$^6$; —C(=O)—O—R$^7$; —O—C(=O)—R$^8$; —NH—C(=O)—R$^9$; —C(=O)—NH$_2$; —C(=O)—NH—R$^{10}$; —C(=O)—NR$^{11}$R$^{12}$; —O—R$^{13}$; —S—R$^{14}$; S(=O)—R$^{15}$; —S(=O)$^{16}$; unsubstituted or at least monosubstituted alkyl; unsubstituted or at least monosubstituted heteroalkyl; unsubstituted or at least monosubstituted cycloalkyl; unsubstituted or at least monosubstituted cycloalkenyl; unsubstituted or at least monosubstituted heterocycloalkyl; unsubstituted or at least monosubstituted heterocycloalkenyl; or unsubstituted or mono- or polysubstituted aryl;

and

R$^6$, R$^7$, R$^8$, R$^9$; R$^{10}$; R$^{11}$; R$^{12}$; R$^{13}$; R$^{14}$; R$^{15}$ and R$^{16}$, mutually independently, in each case denote unsubstituted or at least monosubstituted alkyl; unsubstituted or at least monosubstituted alkenyl or unsubstituted or at least monosubstituted heteroalkyl;

with at least one compound of general formula (III)

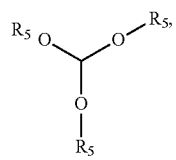

(III)

wherein R$^5$, mutually independently, in each case denotes unsubstituted or at least monosubstituted alkyl;

in the presence of at least one Lewis acid.

2. The process of claim 1, wherein the at least one Lewis acid is a metal-containing compound selected from the group consisting of a) AsX$_3$, GaX$_3$, BX$_3$, BX$_3$.(C$_2$H$_5$)$_2$O, BX$_3$.S(CH$_3$)$_2$, AlX$_3$, (C$_2$H$_5$)$_2$AlX, SbX$_3$, SbX$_5$, SnX$_2$, MgX$_2$, MgX$_2$.O(C$_2$H$_5$)$_2$, ZnX$_2$, BiX$_3$, FeX$_2$, TiX$_2$, TiX$_4$, NbX$_5$, NiX$_2$, CoX$_2$, HgX$_2$, wherein X in each case denotes F, Cl, Br or I, b) BH$_3$, B(CH$_3$)$_3$, GaH$_3$, AlH$_3$, Al(acetate)(OH)$_2$, Al[OCH(CH$_3$)$_2$]$_3$, Al(OCH$_3$)$_3$, Al(OC$_2$H$_5$), Al$_2$O$_3$, (CH$_3$)$_3$Al, Ti[OCH(CH$_3$)$_2$]$_3$Cl, Ti[OCH(CH$_3$)$_2$]$_4$, methylaluminum di-(2,6-di-tert-butyl-4-methylphenoxide), methylaluminum di-(4-brom-2,6-di-tert-butylphenoxide), LiClO$_4$, c) Mg(acetate)$_2$, Zn(acetate)$_2$, Ni(acetate)$_2$, Ni(NO$_3$)$_2$, Co(acetate)$_2$, Co(NO$_3$)$_2$, Cu(acetate)$_2$, Cu(NO$_3$)$_2$, Li(acetate), Zr(acetylacetonate)$_4$, Si(acetate)$_4$, K(acetate), Na(acetate), Cs(acetate), Rb(acetate), Mn(acetate)$_2$, Fe(acetate)$_2$, Bi(acetate)$_3$, Sb(acetate)$_3$, Sr(acetate)$_2$, Sn(acetate)$_2$, Zr(acetate)$_2$, Ba(acetate)$_2$, Hg(acetate)$_2$, Ag(acetate), Tl(acetate)$_3$, d) Sc(fluoromethansulfonate)$_3$, Ln(fluoromethanesulfonate)$_3$, Ni(fluoromethanesulfonate)$_2$, Ni(tosylate)$_2$, Co(fluoromethanesulfonate)$_2$, Co(tosylate)$_2$, Cu(fluoromethanesulfonate)$_2$, and Cu(tosylate)$_2$.

3. The process of claim 1, wherein the at least one Lewis acid is a metal-containing compound selected from the group consisting of AlX$_3$, SnX$_2$, MgX$_2$, ZnX$_2$, BiX$_3$, FeX$_2$, Al[OCH(CH$_3$)$_2$]$_3$, Al(OCH$_3$)$_3$ and Al(OC$_2$H$_5$)$_3$, wherein X in each case denotes F, Cl, Br, or I.

4. The process of claim 3, wherein X denotes Cl.

5. The process of claim 1, wherein the at least one Lewis acid is a metal-containing compound selected from the group consisting of AlCl$_3$, SnCl$_2$, MgCl$_2$, ZnCl$_2$, BiCl$_3$, FeCl$_2$, Al[OCH(CH$_3$)$_2$]$_3$, Al(OCH$_3$)$_3$, and Al(OC$_2$H$_5$)$_3$.

6. The process of claim 1, wherein the molar ratio of the at least one compound of general formula (II) to the at least one compound of general formula (III) is in the range of 5.0:1.0 and 2.5:1.0.

7. The process of claim 1, wherein the concentration of the at least one metal-containing compound in relation to the at least one compound of general formula (II) is in the range of 1 mol-% to 60 mol-%.

8. The process of claim 1, wherein the at least one compound of general formula (II) and the at least one compound of general formula (III) are reacted in at least one inert organic solvent selected from the group consisting of toluene, xylene, ortho-xylene, para-xylene, mesitylene, cyclohexane, cyclopentanone, benzonitrile, chlorobenzene, 1,2-dichlorobenzene, 1,2-dichloroethane, dibutylether, anisol, butylacetate, methylethylketone, methylisobutylketone, pinacolone, dimethylformamide, and acetonitrile.

9. The process of claim 1, wherein the at least one compound of general formula (II) and the at least one compound of general formula (III) are reacted at a temperature in the range of 70° C. to 140° C. for a period in the range of 2 to 20 hours.

10. The process of claim 1, wherein the at least one compound of general formula (II) and the at least one compound of general formula (III) are reacted in an inert solvent, wherein the molar concentration of the at least one compound of general formula (II) is in the range of 1.0 M to 8.0 M.

11. The process of claim 1, wherein R$^5$ denotes unsubstituted C$_{1-5}$ alkyl.

12. The process of claim 1, wherein R$^1$ and R$^3$, mutually independently, in each case denote H, F, Cl, Br, I, unsubstituted or at least monosubstituted C$_{1-12}$ alkyl, unsubstituted or at least monosubstituted C$_{3-8}$ cycloalkyl, or unsubstituted or mono- or polysubstituted aryl; and R$^2$ and R$^4$, in each case denote H.

13. The process of claim 1, wherein R$^1$ and R$^3$, mutually independently, in each case denote a moiety selected from the group consisting of methyl, ethyl, propyl, isopropyl, n-butyl, isobutyl, tert-butyl, n-pentyl, 1,1-dimethylpropyl, 2,2-dimethylpropyl, 3-methylbutyl, hexyl, 2-ethylhexyl, heptyl, octyl, nonyl, decyl, undecyl, dodecyl, cyclopentyl, cyclohexyl, 1,1,3,3,-tetramethylbutyl, sec-butyl, CH$_3$—CH$_2$—C(CH$_3$)$_2$—, and unsubstituted phenyl; and R$^2$ and R$^4$, in each case denote H.

14. The process of claim 1, wherein the compound of general formula (I) is purified and isolated by applying the following steps:

(a) adding an inert organic solvent and water to provide an organic phase and a water phase;

(b) separating the organic phase from the water phase;

(c) optionally washing the organic phase with a 1N aqueous solution of hydrochloric acid;

(d) washing the organic phase with water;

(e) filtering the organic phase to provide a residue and drying the residue.

* * * * *